United States Patent [19]
Robbins et al.

[11] Patent Number: 5,415,857
[45] Date of Patent: * May 16, 1995

[54] HAIR CONDITIONING SHAMPOOS CONTAINING AMINOSILICONE CONDITIONING AGENT

[75] Inventors: Clarence R. Robbins, Martinsville; Amrit M. Patel, Dayton, both of N.J.

[73] Assignee: Colgate-Palmolive Company, New York, N.Y.

[ * ] Notice: The portion of the term of this patent subsequent to Apr. 21, 2009 has been disclaimed.

[21] Appl. No.: 963,214

[22] Filed: Oct. 19, 1992

Related U.S. Application Data

[63] Continuation of Ser. No. 806,679, Dec. 13, 1991, abandoned, which is a continuation of Ser. No. 432,952, Nov. 7, 1989, abandoned, which is a continuation-in-part of Ser. No. 369,361, Jun. 21, 1989, abandoned.

[51] Int. Cl.$^6$ .................. A61K 7/075; A61K 7/08
[52] U.S. Cl. ..................... 424/70.122; 424/70.24; 424/70.28
[58] Field of Search ............ 424/71, 70.122, 70.24, 424/70.28

[56] References Cited
U.S. PATENT DOCUMENTS
5,106,613  4/1992  Hartnett et al. .................. 424/71

Primary Examiner—Thurman K. Page
Assistant Examiner—R. Harrison
Attorney, Agent, or Firm—Richard J. Ancel; Robert C. Sullivan

[57] ABSTRACT

A hair conditioning shampoo, of improved fiber conditioning properties, includes an aminosilicone of the amodimethicone type, of a certain formula, and an aqueous medium for the aminosilicone, which serves as a carrier for it. Preferably, the carrier is an aqueous anionic shampoo medium that also contains a cationic surfactant hair conditioning agent, such as a quaternary ammonium salt, and more preferably it also contains hydrocarbon components, such as microcrystalline wax and petrolatum and/or polyethylene and mineral oil, which promote further improvement in conditioning effects on human hair. The invention is also of hair conditioning processes and combined shampooing and hair conditioning operations, and of processes for manufacturing the invented conditioning shampoos.

19 Claims, No Drawings

HAIR CONDITIONING SHAMPOOS CONTAINING AMINOSILICONE CONDITIONING AGENT

This application is a continuation of Ser. No. 07/806,679, filed Dec. 13, 1991, now abandoned, which is a continuation of Ser. No. 07/432,952, filed Nov. 7, 1989, now abandoned, which is a continuation-in-part of Ser. No. 07/369,361, filed Jun. 21, 1989, now abandoned.

This invention relates to fiber conditioning compositions. More particularly, it relates to such composition which are shampoos that include certain aminosilicones which, together with cationic surfactant fiber conditioning agents, such as quaternary ammonium salts, improve fiber conditioning significantly and, especially in the case of anionic synthetic organic detergent shampoos, result in excellent conditioning of human hair while it is being cleaned.

Fiber conditioning compositions, such as fabric conditioning detergent compositions and non-detergent conditioning compositions, for treating washed fibrous materials, which condition washed fabrics by making them softer and less likely to hold static charges after being dried in an automatic laundry dryer, have been marketed, and have contained cationic conditioning agents, such as quaternary ammonium salts, and such quaternary ammonium compounds have also been included in hair rinses. Aminosilicones and amodimethicones have been suggested as hair conditioning components of shampoos and so have various hydrocarbons, such as petrolatum and mineral oils. Anionic synthetic organic detergents, such as higher fatty alcohol sulfates and higher fatty alcohol polyethoxy sulfates, have been employed in shampoos, sometimes in conjuntion with quaternary ammonium halides. In U.S. Pat. No. 5,051,250, shampoos are described which contain anionic detergent, cationic fiber conditioning surface active agent, polyethylene and solubilizing liquid hydrocarbon (mineral oil), in which the combination of polyethylene and mineral oil improves the hair conditioning action of the shampoo. However, it is applicants' belief that prior to their present invention their conditioning shampoos based on anionic synthetic organic detergent(s) and cationic hair conditioning surfactant, and the unexpectedly improved conditioning effects resulting from such combination had not been previously noted or obtained by others.

The closest prior art known to applicants appears to be U.S. Pat. Nos.: 4,559,227; 4,563,347; 4,601,902; 4,704,272; 4,710,314; and 4,749,732. U.S. Pat. No. 4,559,227 discloses aminosilicone polymers of structure similar to that of those of the present invention (see Example 7 of the patent, for example), and U.S. Pat. No. 4,710,314 describes hair conditioning shampoos that contain amodimethicone (an aminosilicone) and cationic surfactant conditioner. However, neither describes applicants' preferred aminosilicones and neither would lead one to believe that applicants' compositions, which contain such an aminosilicone, would be significantly better hair conditioning shampoos than similar compositions based on aminosilicones of similar structure (but different).

In accordance with the present invention a fiber conditioning composition, which is of improved fiber conditioning characteristics, comprises an aminosilicone of the formula

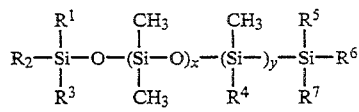

wherein $R^1$, $R^2$, $R^3$, $R^5$, $R^6$ and $R^7$ are alkyls of 1 to 6 carbon atoms, and most preferably of 1 carbon atom each, $R^4$ is $-R^8-NH-CH_2CH_2-NH_2$, $R^8$ is alkylene of 3 to 6 carbon atoms, and most preferably is an isobutyl group, x is an average number in the range of 200 to 10,000, and more preferably above 500 and less than 10,000, and most preferably 750–800, and y is an average number in the range of 1 to 10, and more preferably less than 5, and most preferably 1, which is of an amine equivalent in the range of 4,000 to 60,000, and a carrier for the aminosilicone. The carrier is normally liquid and is often a detergent composition, preferably a shampoo, and when it is a shampoo it preferably includes a cationic fiber conditioning agent, such as a quaternary ammonium salt. The presence of the quaternary ammonium salt appears to assist in the emulsification of the aminosilicone into the aqueous system, thereby helping to stabilize the shampoo, and also helps to make the aminosilicone more effective in its hair conditioning function, despite the presence of anionic synthetic organic detergent, which is usually present in such shampoo in much greater proportion than the conditioning agents.

The aminosilicones of this invention (see the chemical formula above) are preferably of amine equivalents in the range of 4,000 to 60,000 and more preferably such amine equivalent is of 10,000 or 20,000 to 40,000, with average x's in the range of 200 to 10,000 and more preferably above 500 and less than 10,000, and most preferably between 750–800, and with average y's in the range of 1 to 10 and more preferably less than 5, and most preferably 1. They may also contain up to 25% cyclomethicone, which is used as a processing aid in their manufacture, but they may, desirably, contain less than this amount since cyclomethicone is not desirable in the formulations of this invention. The amine equivalent is numerically equal to the weight in grams of polymer that contains 14 grams of amine nitrogen. In the preferred compositions of the present invention the aminosilicone polymer will be one obtained from Dow-Corning Corporation, which is designated as aminosilicone B in Table 2 below. Such aminosilicone is of a low charge density and amine content, with the amine equivalent being 30,000. In this polymer, the structure of which is illustrated above, $R^1$, $R^2$, $R^3$, $R^5$, $R^6$, and $R^7$ are all methyl groups, and $R^8$ is an isobutyl group. The viscosity of this material is 7500±1000 cps. Another such aminosilicone, designated herein as Dow-Corning aminosilicone A in Table 2 below is also useful but is not as effective as aminosilicone B, which is of a higher molecular weight and a lower charge density. Other aminosilicones made by Dow-Corning, identified as Silicones C, D and E in Table 2 below, while of similar formulas, are of different charge densities (charge density is inversely related to amine equivalent), are less effective, and unacceptable as hair conditioning agents in applicants' compositions.

The carrier for the aminosilicone may be any suitable carrier, preferably liquid and aqueous, and often will include a surface active material (surfactant) or a detergent, which will help maintain the aminosilicone emulsified, dispersed or suspended in the aqueous medium, and will help to prevent phase separations and settling out of the aminosilicone and other components of the composition. Very preferably, the carrier will be a shampoo and such shampoo will be useful to wash the hair and condition it so that after washing (and removal of hair oils) the hair will not be difficult to manage, which is often observed after shampooing, due to the shampooing removing from the hair substances that have conditioning properties. Instead of shampoos serving as carriers for the aminosilicones other compositions may also be employed, including solvents, gels, pastes, cremes, lotions, emulsions, sprays, etc., and the aminosilicones may be applied to fibrous materials and to the hair in any normal manners. Because bases for such various forms of cosmetic materials are well known they will not be specifically recited here, which is considered to be unnecessary because those skilled in the art will readily be aware of their compositions or can obtain formulas thereof from any of various texts in the field of cosmetics, such as *Modern Cosmeticology*.

The cationic surface active fiber conditioning agents, which may be considered to be secondary conditioning agents in the invented fiber conditioning compositions, are preferably quaternary ammonium salts, although other surface active compounds with fiber conditioning properties may also be employed, at least in part. Thus, imidazolinium salts and betaines, and such cationic materials as are described in U.S. Pat. No. 4,000,077 may be substituted for at least some of the quaternary ammonium salt, as may be complexes of cationic and anionic surfactants, such as have been described in U.S. Pat. Nos. 4,786,422; 4,888,119; and 4,929,367.

The preferred quaternary ammonium salts are of the formula $R^9 R^{10} R^{11} R^{12} N^+ X^-$, wherein at least one of the R groups is lower alkyl and at least one is higher alkyl, with the others being higher and/or lower alkyl. Preferably $R^9$ is lower alkyl, such as of 1 to 4 carbon atoms, $R^{10}$ and $R^{11}$ are higher alkyls of 10 to 40 carbon atoms, $R^{12}$ is such a higher alkyl or lower alkyl, and $X^-$ is a salt-forming anion, such as halide, lower alkosulfate or lower carboxylic acid radical, e.g., chloride, bromide, methosulfate, ethosulfate, citrate or acetate. The lower alkyl will preferably be of 1 to 3 carbon atoms, more preferably being of 1 or 2 carbon atoms, and most preferably, in most cases, will be methyl, and the higher alkyl will preferably be of 10 to 22 carbon atoms, more preferably 12 to 18 or 20 carbon atoms, most preferably of 14 to 18 carbon atoms, e.g., 16 or about 16 carbon atoms. The anion is preferably a halogen, such as chlorine, bromine or iodine, with chlorine and bromine being preferred and with chlorine being more preferred.

The number of lower alkyls on the quaternary nitrogen will preferably be 1 or 2 and the number of higher alkyls will usually be 2 or 3. It has been found to be desirable to have at least 30 carbon atoms in the quaternary ammonium salt and preferably at least 34. The most preferred higher alkyl is cetyl, the most preferred lower alkyl is methyl, and the most preferred quaternary ammonium halide is tricetyl methyl ammonium chloride. Nevertheless, it is within the invention to employ other quaternary ammonium halides, such as distearyl dimethyl ammonium chloride, dilauryl dimethyl ammonium bromide, stearyl cetyl dimethyl ammonium chloride, trimyristyl ethyl ammonium bromide and trilauryl ethyl ammonium chloride, and other fiber and hair conditioning cationic surfactants as at least part of the fiber and/or hair conditioning cationic surfactant (surfactant is short for surface active agent) content of the present compositions.

As was indicated previously, the fiber conditioning compositions of the invention may be in various suitable forms, although they are preferably in aqueous liquid form. The compositions may be used directly or may be dissolved and/or dispersed in water or other aqueous medium. Preferred compositions are shampoos, which will usually include a synthetic anionic organic detergent and water, but the preferred aminosilicones may also be included in non-detersive formulations with suitable carriers, such as in thickened aqueous media, emulsions, microemulsions and stable dispersions, preferably with cationic conditioning agent, too. Optionally, amphoteric, ampholytic, zwitterionic and nonionic detergents and surfactants may be utilized in the mentioned shampoos instead of or with the anionic detergent(s). Various suitable such detergents and surfactants are listed and described in *McCutcheon's Detergents and Emulsifiers*, North American Edition, 1984.

The preferred anionic detergents, which are also described in the McCutcheon book, may be designated as "sulf(on)ated". Such are water soluble lipophilic sulfates and/or sulfonates of 8 to 22 carbon atoms, preferably of 10 to 20 carbon atoms, more preferably of 10 to 16 or 18 carbon atoms, and most preferably of 12 to 16 or 18 carbon atoms. Among such anionic detergents there may be mentioned, as exemplary thereof, higher ($C_{12-18}$) alkyl sulfates, higher paraffin sulfonates, higher olefin sulfonates, higher fatty acid monoglyceride sulfates, higher fatty alcohol lower alkoxy (and polyoxy) sulfates, linear higher alkyl benzene sulfonates, and dialkyl sulfosuccinates. The most preferred of these anionic detergents for the present shampoos are the higher alkyl sulfates of 12 to 16 carbon atoms and the higher alkyl lower alkoxy sulfates of 16 to 18 carbon atoms (preferably with the higher alkyl thereof being lauryl and with 2 or 3 ethoxy groups per mole). However, such alkyls may be of 12 to 16 carbon atoms and the alkoxy content may be of 1 to 20 per mole, such as 2 to 6 ethoxies per mole. A most preferred higher fatty alcohol sulfate is lauryl sulfate and a particularly preferred higher fatty alcohol poly-lower alkoxy sulfate is di- or triethoxylated lauryl alcohol sulfate. Most preferably the anionic detergent will be a mixture of higher alkyl sulfate and higher alkyl ether sulfate, with either being present in greater or equal proportion, and with the ratio of amounts of such components being in the range of 10:1 to 1:10 or 7:1 to 1:7, e.g., 1:5 to 5:1, when both such anionic detergents are present.

The anionic detergents will be employed in the forms of their water soluble salts, which will usually be salts of alkali metals (sodium, potassium), ammonium, amines (such as dimethylamine and trimethylamine) or lower alkanolamines (such as triethanolamine, diethanolamine and monoethanolamine). Exemplary of useful detergents are ammonium lauryl sulfate, sodium lauryl diethoxy sulfate, ammonium lauryl triethoxy sulfate, sodium alpha $C_{16}$ olefin sulfonate, sodium $C_{14}$ paraffin sulfonate, sodium coco monoglyceride sulfate, triethanolamine cetyl sulfate and dimethylamine myristyl sulfate. However, for best results it is preferred to utilize higher alkyl sulfate, higher alkyl poly-lower alkoxy sulfate or a mixture of such higher alkyl sulfate and such higher alkyl ether sulfate, such as lauryl sulfate and lauryl diethoxy sulfate or lauryl triethoxy sulfate, often with the higher alkyl sulfate being present in greater proportion and in ammonium, triethanolamine and/or sodium salt form.

The water employed in the aqueous compositions of the invention, including the preferred shampoos, will preferably be deionized water of a hardness content less than 10 parts per million, as $CaCO_3$, but other waters may also be utilized when circumstances require. So as to ensure that the invented compositions are free of microorganisms it is preferred to use irradiated deionized water, and the various mixing vessels, tanks, piping and containers employed will be maintained in clean condition.

In addition to the required components of the invented conditioning compositions, including the shampoos which are preferred embodiments therof, there may also be present in such compositions various adjuvants which are known in the art to impart desirable properties or which have been determined by the present inventors or their fellow researchers to have desirable effects when incorporated in the invented compositions. Among such adjuvants may be mentioned: paraffins, petrolatums, microcrystalline waxes, isoparaffins mineral oils and polyethylenes, all of which have been described in application Ser. No. 07/369,361, now abandoned and in our U.S. Pat. No. 5,051,250, and which are useful to further improve the conditioning effects of the basic compositions of the present invention. Such materials, although not required components of the basic compositions of this invention, are very useful adjuvants and significantly improve the conditioning activities of the invented compositions. When the polyethylene is being used it will be accompanied by a solubilizing hydrocarbon, such as mineral oil, although other liquid or near liquid hydrocarbons can also be employed for that purpose. Other useful adjuvants or non-required components of the conditioning compositions and shampoos include higher fatty acid esters of lower alcohols, lower fatty acid esters of higher alcohols, and higher fatty acid esters of higher fatty alcohols, and mixtures thereof, as described in U.S. patent application Ser. No. 07/369,361, now abandoned; thickeners, such as lower alkyl celluloses and hydroxy-lower alkyl celluloses, e.g., methyl cellulose and hydroxypropyl methyl cellulose, and gums, such as xanthan gum, which may also act as stabilizers for the aqueous compositions; foam modifiers and improvers, such as betaines, higher fatty acid triglycerides, and higher fatty acid alkanolamides, e.g., coco amidopropyl betaine, $C_{18-36}$ acids triglycerides and lauric monoethanolamide; pearlescing agents, such as ethylene glycol mono- and distearates; anti-dandruff agents, such as zinc pyrithione; viscosity control agents, such as propylene glycol and sodium chloride; preservatives and antioxidants; anti-freezes, such as ethylene glycol; sequestrants, such as EDTA; pH adjusters, such as citric acid and citrates; colorants (dyes and water dispersible pigments); and solvents, such as ethanol and isopropanol.

The proportions of the various components of the invented compositions are such as to produce the desired fiber conditioning effects and increases in such effects. Such improvements are obtained when the proportion of cationic fiber conditioning surfactant is sufficient to add conditioning to the conditioning effect of the aminosilicone, and also is enough to improve the dispersion of the aminosilicone so as to stabilize it in the aqueous medium. The proportion of anionic detergent is such as to clean the hair or other fiber thoroughly but also is such that the aminosilicone and cationic conditioning surfactant can deposit on the fiber or hair from the comparatively strong aqueous detergent medium. The proportion of hydrocarbon materials is such that it improves the conditioning effects of the aminosilicone and cationic conditioning agent. Finally, such proportions are those which will allow the composition to be stable on storage, non-settling and non-separating, and the water content will be sufficient to form such a stable continuous aqueous medium in which the other components will be contained in stable form.

For non-shampoo conditioning compositions the proportions of aminosilicone, cationic surfactant and water will normally be in the ranges of 0.1 to 10%, 0.1 to 10% and 50 to 99%, respectively, with any difference being of adjuvant(s) and surfactant, if present. When the surfactant is present in such compositions it will be in a proportion in the range of 0.5 to 20%.

For shampoos and other cleaning compositions that are desirably fiber conditioning the proportion of aminosilicone will usually be in the range of 0.3 to 5%, preferably 0.5 to 5%, more preferably 1 to 3%, e.g., about 1, 1.5, 2 or 3%. The percentage ranges for the cationic surfactant conditioner will usually be 0.1 to 5%, preferably 0.1 to 3%, more preferably 0.2 to 2% and most preferably 0.3 to 1%, e.g., 0.5%. The percentage of anionic detergent is normally 5 to 30%, preferably 8 to 25%, more preferably 10 to 20% and most preferably 12 to 18%, e.g., 15%. When mixed alkyl sulfate and alkyl ethoxy sulfate anionic detergents are present the proportions will normally be 10 to 15% of the alkyl sulfate and 2 to 5% of the alkyl ether sulfate, although the proportions can also be reversed, in some circumstances. The water content will normally be in the range of 50 to 85%, preferably 60 to 90% and more preferably 65 to 80%, e.g., about 70, 73 or 75%. The adjuvant content will normally be 0.1 to 30%, preferably 0.5 to 30%, preferably 0.5 to 20% and more preferably 3 to 15%, e.g., about 8 or 9%.

When a supplementing hydrocarbon conditioning agent is present the percentage thereof will be in the range of 0.5 to 20%, preferably 1 to 10% and more preferably 1.5 to 5%. Preferred hydrocarbon component contents are 0.1 to 5% of microcrystalline wax with 0.1 to 3% of paraffin, more preferably 0.5 to 3% and 0.5 to 2%, respectively. When polyethylene and mineral oil are present to add their supplementing conditioning effect the proportions will normally be in the ranges of 0.2 to 5% of the polyethylene and 0.1 to 10% of mineral oil, preferably 0.2 to 2%, and 0.2 to 8%, respectively and more preferably 0.3 to 1% and 0.5 to 5%, respectively.

For non-aqueous compositions the required, optional and adjuvant components will normally be in the same ranges of proportions as in the aqueous compositions, with the water removed. The aqueous medium may be omitted or replaced, in whole or in part, by another solvent or liquid medium, e.g., ethanol or isopropanol.

As had been indicated previously, although the fiber conditioning and hair conditioning compositions of this invention may be in various physical forms preferably they are in liquid form and a preferred embodiment of the invention is a hair conditioning shampoo. Such compositions should be stable chemically and physically to be acceptable in the marketplace. They should not deteriorate to an unacceptable extent on storage, and will not have components settle out or phases separating during storage. Also, the shampoos will be of desirable viscosities, so as to be pourable and yet will not be so thin that they run uncontrollably. The desired viscosity range is 1,000 to 15,000 centipoises at room temperature (25° C.), preferably 3,000 to 6,000 centipoises, and more preferably the viscosity will be of about 3,500 or 4,000 centipoises at room temperature. The invented shampoos are non-settling and non-separating, and do not chemically deteriorate on storage, as has been established by accelerated aging tests at elevated temperatures. The shampoo viscosity may change slightly on storage but such an increase does not significantly affect the shampoo's properties. Also, the desired use viscosity can be planned and the shampoo can be designed to have the desired viscosity when it is normally expected to be used by the consumer.

The improved hair conditioning obtained by use of the invented compositions, compared to controls, from which any of the aminosilicone, cationic conditioner, or hydrocarbon conditioner has been omitted, is quite noticeable to the casual user of the shampoo or other invented conditioning composition, and is measurable in standard tests that are used to evaluate conditioning and its components, including ease of wet combing, ease of dry combing, manageability, static charge retention and flyaway. The casual shampooer will note that the hair is easier to comb after shampooing, in both wet and dry states, compared to control hair washed with a shampoo that is not under the invention (with one or more components missing from it). Scientific tests also prove that the force needed to move a comb through a standard hair tress after treatment (shampooing) of the hair with an invented shampoo, and rinsing, is measurably less than that when such control is employed in the same manner. Such results are confirmed by panel tests, in which several experienced evaluators, using both the experimental and control products in blind tests, evaluate them for such combing ease, manageability and static characteristics and effects.

Uses of the invented compositions, including shampoos, are not required to be different from normal uses of hair conditioning shampoos and other conditioning compositions. Conditioning agents may be applied at room temperature or at somewhat elevated temperatures in normal quantities and may be left on the hair for different lengths of time, depending on the extent of conditioning desired. Usually the conditioning agent and the hair will be at a temperature in the range of 15° to 50° C., preferably 20° to 40° C., and the conditioning composition will be in contact with the hair for from 30 seconds to ten minutes, preferably one to five minutes. The amount of composition applied will normally be in the range of 0.1 to 25 grams, often being 0.2 to 10 g. or 0.5 to 2 or 5 g., on the basis of the non-aqueous and non-solvent components of the compositions. On the basis of the shampoo which may be employed such application raltes may be in the range of 0.5 to 50 grams, often 2 to 15 or 20 grams and frequently five or ten grams per use. The applied composition may be brushed and/or combed through the hair and may be subsequently washed out, may be allowed to remain on the hair or may be partially removed, as by towelling. When the shampoo is employed to wash and condition the hair it will be rinsed off with water after remaining on the hair as an aqueous foam for a sufficient length of time, usually 1 to 5 minutes, to satisfactorily condition the hair, and may then be wet combed, dried, as by blow drying, and dry combed or brushed to the desired style.

To manufacture the present compositions, including shampoos, no complex procedures have to be followed, but to obtain best stability and greatest conditioning activity, after storage of the invented compositions, it will be desirable to form a dispersion of the water soluble lipophile sulfate and/or sulfonate and adjuvants in water at an elevated temperature, such as 70° to 90° C., dissolve and/or disperse cationic conditioning agent, such as quaternary ammonium salt, with any lipophilic materials, such as hydrocarbons, including polyethylene, mineral oil, microcrystalline wax, petrolatum, paraffin and isoparaffin as a melt or liquid mix at elevated temperature, and admix the two pre-mixes, at such elevated temperature, after which the heated aminosilicone may be admixed with the resulting mix, with the various mixings taking place with the portions to be mixed at approximately the same temperatures. It is important that the aminosilicone be mixed in after the main pre-mixing; otherwise it may separate out or form an unstable composition. When adjuvants are present those which are water soluble and/or dispersible may be mixed in with the aqueous phase materials and those which are not water soluble or dispersible in the aqueous medium, may be blended in with the lipophilic materials, such as the hydrocarbons, or in some instances may be added to the mixture of the hydrophilic and lipophilic materials either before or after cooling to room temperature. Normally perfume will be added to the other mixed components after cooling to room temperature and the aminosilicone will be added at elevated temperature and before such cooling. The perfume is added to the cooled composition to avoid losses thereof due to volatilizations of components and to prevent and heat degradation. When the procedure described is not followed, as when the various components of the compositions are blended indiscriminately, unstable products may result, which can separate or settle out on storage, and such unstable compositions tend to have poorer conditioning properties than the stable conditioning compositions and shampoos that are made according to the invented procedure.

The following examples illustrate but do not limit the invention. Unless otherwise indicated all parts are by weight and all temperatures are in degrees Centigrade.

EXAMPLE 1

| | Percent (by weight) | | | | |
|---|---|---|---|---|---|
| Component | A | B | C | D | E |
| Part 1 | | | | | |
| Deionized water | 75.89 | 75.64 | 75.14 | 74.54 | 73.64 |
| *Natrosol TM 250 HHR | 0.45 | 0.45 | 0.45 | 0.45 | 0.45 |
| **Natrosol 330 CS | 0.15 | 0.15 | 0.15 | 0.15 | 0.15 |
| Ammonium lauryl sulfate | 12.50 | 12.50 | 12.50 | 12.50 | 12.50 |
| Sodium lauryl diethoxy sulfate | 2.50 | 2.50 | 2.50 | 2.50 | 2.50 |
| Part 2 | | | | | |
| ***$C_{18-36}$ acid triglyceride | 0.75 | 0.75 | 0.75 | 0.75 | 0.75 |
| Ethylene glycol distearate | 0.75 | 0.75 | 0.75 | 0.75 | 0.75 |
| Stearyl stearate | 0.35 | 0.35 | 0.35 | 0.35 | 0.35 |
| Propylene glycol, U.S.P. | 0.50 | 0.50 | 0.50 | 0.50 | 0.50 |
| Lauric monoethanolamide | 3.50 | 3.50 | 3.50 | 3.50 | 3.50 |
| Tricetyl methyl ammonium chloride | 0.50 | 0.50 | 0.50 | 0.50 | 0.50 |
| Others | | | | | |

-continued

| Component | Percent (by weight) | | | | |
|---|---|---|---|---|---|
| | A | B | C | D | E |
| ****Preservative (Germaben II) | 0.50 | 0.50 | 0.50 | 0.50 | 0.50 |
| Dye (1% aqueous solution) | 0.10 | 0.10 | 0.10 | 0.10 | 0.10 |
| + Sodium chloride | 0.30 | 0.30 | 0.30 | 0.30 | 0.30 |
| ++ Citric acid | 0.01 | 0.01 | 0.01 | 0.01 | 0.01 |
| Dow-Corning ™ Silicone "B" | 0.75 | 1.00 | 1.50 | 2.00 | 3.00 |
| Perfume | 0.50 | 0.50 | 0.50 | 0.50 | 0.50 |
| | 100.00 | 100.00 | 100.00 | 100.00 | 100.00 |

*hydroxyethyl cellulose (Hercules Corp.)
**Hydroxyethyl cellulose (Hercules Corp.)
***Syncrowax ™ HGC-L (mf'd. by Croda Corp.)
****Mf'd. by Sutton Laboratories, Inc.
+ Sodium chloride (viscosity regulator, can be employed up to 0.5%, to increase shampoo viscosity).
++ pH adjuster, can be employed, up to 0.1%, to lower pH, or sodium citrate can be employed, up to 0.1%, to raise pH.

The shampoo of the invention is made by charging the formula amount of water to a primary mixing vessel, starting mixing, and slowly sprinkling in the formula amounts of the Natrosols. Mixing is continued until the Natrosols are dissolved, while the medium is being heated to about 50° C. Heating is continued until the temperature is in the range of 80° to 85° C., after which the heat is turned down and the mixing is continued. The formula amounts of ammonium lauryl sulfate and sodium lauryl diethoxy sulfate are then added. During the time that the Part 1 components are being prepared the Part 2 components, including $C_{18-36}$ acid triglyceride, ethylene glycol distearate, stearyl stearate, propylene glycol, lauric monoethanolamide and tricetyl ammonium chloride, are either added separately or together to a separate container and are heated, with mixing, in such container until a uniform melt or solution is obtained at a temperature in the 80° to 85° C. range. With both Parts 1 and 2 at about the same elevated temperature, Part 2 is added to Part 1 in the main mixing vessel, with care being taken to avoid foam formation during admixing. After the admixing is completed the heat is turned off and mixing is continued for another ten minutes, after which the aminosilicone (Dow-Corning Silicone "B") is mixed in and mixing is continued for another ten minutes. When the mix is cooled to 39° C., the formula amounts of perfume, preservative and dye solution are added, with mixing, and sodium chloride and citric acid (or sodium citrate) are added in such amounts as are sufficient to bring the viscosity to about 4,000 centipoises at 25° C., and sodium chloride and citric acid (or sodium citrate) are then added if the viscosity is too low, outside the 4,000 to 6,000 centipoise range (measured on a Brookfield RVTD viscometer, with spindle No. 4, rotating at 20 r.p.m), and if the pH is off specification (although in some circumstances the pH may be as low as 5 or as high as 8).

After the manufacturing of products 1/A, 1/B, 1/C, 1/D and 1/E, they are evaluated for hair conditioning properties, using standard dry combing and wet combing evaluation techniques, such as are described in our U.S. Pat. No. 5,051,250. The results of such tests are shown in Table 1.

TABLE 1

| Test | 1/A | 1/B | 1/C | 1/D | 1/E |
|---|---|---|---|---|---|
| ***Evaluation for ease of wet combing | 4-5 | 6-7 | 7-8 | 8-9 | 10-11 |
| ***Evaluation for ease of dry combing | 3-4 | 5-6 | 5-6 | 6-7 | 7-8 |

***Evaluations are on a scale of 1-10, with 1 being minimum conditioning (maximum resistance to combings) and 10 being maximum conditioning (minimum resistance to combings).

The rating of 11 for Composition 1/E indicates conditioning and ease of wet combing that are better than what had theretofore been considered to be obtainable.

A control shampoo is made of the same formula as those of this example, with the exception that the aminosilicone is omitted and is replaced by water. Both wet combing and dry combing ratings for such control shampoo are 1-2, which illustrate the great improvement in conditioning effect obtained and its dependence on the presence of the particular described aminosilicone. When other aminosilicones, such as Dow-Corning Silicones "C" and "D" of similar general formula but of higher charge density, and in some cases lower molecular weight, are substituted for the Silicone "B" significantly lower values in conditioning evaluations result. Also, when the formulas are modified by additions of microcrystalline wax (m.p.=82° C.) and petrolatum, using 0.2 to 1% of microcrystalline wax, such as 0.5%, and 0.2, to 1.5% of petrolatum, such as 0.7%, with water contents being decreased to compensate, dry combing ratings are increased significantly for such modifications of Compositions 1/C, 1/D and 1/E. More importantly, significantly less flyaway hair is observed for all of these hydrocarbon containing compositions.

EXAMPLE 2

| Component | Percent (by weight) | | |
|---|---|---|---|
| | A | B | C |
| Irradiated deionized water | 73.73 | 73.93 | 73.23 |
| Natrosol 250 HHR | 0.37 | 0.45 | 0.45 |
| Natrosol 330 CS | 0.13 | 0.45 | 0.15 |
| Ammonium lauryl sulfate | 12.50 | 12.50 | 12.50 |
| Sodium lauryl diethoxy sulfate | 2.50 | 2.50 | 2.50 |
| Microcrystalline wax (m.p. = 82° C.) | 1.00 | 0.20 | 0.20 |
| $C_{18-36}$ acid triglyceride | 0.75 | 0.75 | 0.75 |
| Snow white petrolatum | 1.00 | 0.20 | 0.20 |
| Tricetyl methyl ammonium chloride | 0.50 | 0.50 | 0.50 |
| Ethylene glycol distearate | 0.75 | 0.75 | 0.75 |
| Propylene glycol, U.S.P. | 0.50 | 0.50 | 0.50 |
| Lauric monoethanolamide | 3.50 | 3.50 | 3.50 |
| Stearyl stearate | 0.35 | 0.35 | 0.35 |
| Others | | | |
| Dow-Corning Silicone "B" | 1.00 | 2.00 | 3.00 |
| Sodium chloride | 0.10 | 0.10 | 0.10 |
| Preservative | 0.50 | 0.50 | 0.50 |
| Citric acid | 0.01 | 0.01 | 0.01 |
| Dye solution (0.5% aqueous solution) | 0.31 | 0.31 | 0.31 |
| Perfume | 0.50 | 0.50 | 0.50 |
| | 100.00 | 100.00 | 100.00 |

Compositions 2/A, 2/B and 2/C are made according to the procedures described in Example 1 and are tested according to the procedures also described therein. The products are stable shampoos, which can last a year or more under normal conditions without deteriorating or losing conditioning powers, and without separating or settling out of component materials. The three shampoos are each adjusted to be of a viscosity in the range of 3,500 to 4,000 centipoises at 25° C., with such adjustment being made by addition of sodium chloride to thicken the shampoo to the desired viscosity. Also, pH's thereof are in the range of 6 to 7, normally being about 6.5, with pH adjustment being effected by addition of citric acid and/or sodium citrate, as appropriate.

When the shampoos are employed to wash and simultaneously condition human hair, evaluations of such hair after washing and rinsing (and drying when appropriate) show that the products made are excellent conditioning shampoos. The ratings (on the same bases as described in Example 1) for wet combing and dry combing for both 2/A and 2/B are 9–10 and wet combing and drying combing ratings for 2/C are both 10–11. Thus, these examples illustrate that when more of the special aminosilicones of this invention is utilized conditioning will be improved. Additionally, it is shown that when microcrystalline wax and petrolatum are present, a lesser proportion of the aminosilicone may be employed, and conditioning corresponding to that obtained from the composition containing more aminosilicone and less microcrystalline wax and petrolatum is achievable. Thus, it would be expected that even better conditioning than 10–11 would be obtained by further increasing the microcrystalline wax and petrolatum contents of Formula 2/C, but care should be taken to avoid any excessive waxy feel of the conditioned hair.

Another advantage of the present invention is that the invented shampoos, although containing significant proportions of very effective anionic detergent(s), do not prevent the deposition of the contained conditioning agents onto the hair or other fibers to be conditioned. Also, although the conditioning agents are substantive to the hair and are not removed from it by the anionic detergent(s) during shampooing, they do not tend to build up excessive deposits on the hair due to repeated shampooings of the hair with the conditioning shampoos, and do not thereby tend to make the hair objectionably greasy. In summary, the conditioning agents, particularly the aminosilicones, sufficiently adhere to the hair from aqueous solutions of the present shampoo components during shampooing but do not objectionably build up deposits on the hair that would tend to make it greasy or would otherwise adversely affect its physical properties.

EXAMPLE 3

| Component | Percent (by weight) | | | | | | | |
|---|---|---|---|---|---|---|---|---|
| | A | B | C | D | E | F | G | H |
| Water (irradiated, deionized) | 73.13 | 68.13 | 68.13 | 70.63 | 73.13 | 73.13 | 69.13 | 71.13 |
| Natrosol 250 HHR | 0.37 | 0.37 | 0.37 | 0.37 | 0.37 | 0.37 | 0.37 | 0.37 |
| Natrosol 330 CS | 0.13 | 0.13 | 0.13 | 0.13 | 0.13 | 0.13 | 0.13 | 0.13 |
| Ammonium lauryl sulfate | 15.00 | — | — | 2.50 | — | — | 12.50 | 12.50 |
| °Ammonium laurethoxy sulfate | — | 20.00 | — | — | — | 7.50 | — | — |
| Sodium laurethoxy (2 EtO) sulfate | — | — | — | — | — | 7.50 | 2.50 | 2.50 |
| Sodium alpha $C_{12-16}$ olefin sulfonate | — | — | — | — | 15.00 | — | — | — |
| Cocoamidopropyl betaine | — | — | — | — | — | — | 3.50 | — |
| Sodium decethoxy (3 EtO) sulfate | — | — | 20.00 | 15.00 | — | — | — | — |
| Microcrystalline wax (m.p. = 82° C.) | 1.00 | 1.00 | 1.00 | 1.00 | 1.00 | 1.00 | 1.00 | 1.00 |
| $C_{18-36}$ acid triglyceride | 0.75 | 0.75 | 0.75 | 0.75 | 0.75 | 0.75 | 0.75 | 0.75 |
| Petrolatum (Snow white) | 0.75 | 0.75 | 0.75 | 0.75 | 0.75 | 0.75 | 0.75 | 0.75 |
| Tricetyl methyl ammonium chloride | 0.50 | 0.50 | 0.50 | 0.50 | 0.50 | 0.50 | 0.50 | 0.50 |
| Ethylene glycol distearate | 0.75 | 0.75 | 0.75 | 0.75 | 0.75 | 0.75 | 0.75 | 0.75 |
| Propylene glycol, U.S.P. | 0.50 | 0.50 | 0.50 | 0.50 | 0.50 | 0.50 | 0.50 | 0.50 |
| Lauric monoethanolamide | 3.50 | 3.50 | 3.50 | 3.50 | 3.50 | 3.50 | 3.50 | 3.50 |
| Stearyl stearate | 0.35 | 0.35 | 0.35 | 0.35 | 0.35 | 0.35 | 0.35 | 0.35 |
| Aminosilicone (Dow-Corning "B") | 1.50 | 1.50 | 1.50 | 1.50 | 1.50 | 1.50 | 1.50 | 1.50 |
| °°Climbazole | — | — | — | — | — | — | — | 0.50 |
| °°°Piroctone olamine | — | — | — | — | — | — | — | 0.50 |
| °°°°Zinc pyrithione | — | — | — | — | — | — | — | 1.00 |
| Sodium chloride | 0.20 | 0.20 | 0.20 | 0.20 | 0.20 | 0.20 | 0.20 | 0.20 |
| Preservative (Germaben II) | 0.50 | 0.50 | 0.50 | 0.50 | 0.50 | 0.50 | 0.50 | 0.50 |
| Sodium citrate | 0.01 | 0.01 | 0.01 | 0.01 | 0.01 | 0.01 | 0.01 | 0.01 |
| Aqueous dye solution (1% concentration) | 0.31 | 0.31 | 0.31 | 0.31 | 0.31 | 0.31 | 0.31 | 0.31 |
| Perfume | 0.75 | 0.75 | 0.75 | 0.75 | 0.75 | 0.75 | 0.75 | 0.75 |
| | 100.00 | 100.00 | 100.00 | 100.00 | 100.00 | 100.00 | 100.00 | 100.00 |

°of 1–3 ethoxies, e.g., 2 EtO
°°anti-dandruff agent, mf'd. by Bayer
°°°anti-dandruff agent, mf'd. by Hoechst, as Octopirox
°°°°anti-dandruff agent, mf'd. by Olin Industries Compositions A–H of this example are made by the procedure previously described in Examples 1 and 2. The various compositions made, all of which are within the present invention, all exhibit improved hair conditioning properties, including easier combing, better manageability, less flyaway (which is attributed in part to the presence of the microcrystalline wax and petrolatum in all the formulas), and repeated shampooings of the compositions do not leave objectionable gummy deposits on the hair, such as can result from employing cationic gum conditioners instead of the described aminosilicones.

EXAMPLE 4

| Component | Percent (by weight) | | |
|---|---|---|---|
| | A | B | C |
| Irradiated deionized water | 73.63 | 73.53 | 73.13 |
| Natrosol 250 HHR | 0.37 | 0.45 | 0.45 |
| Natrosol 330 CS | 0.13 | 0.15 | 0.15 |
| Ammonium lauryl sulfate | 12.50 | 12.50 | 12.50 |
| Sodium lauryl diethoxy sulfate | 2.50 | 2.50 | 2.50 |
| Microcrystalline wax (m.p. = 82° C.) | 1.00 | — | 0.20 |
| $C_{18-36}$ acid triglyceride | 0.75 | 0.75 | 0.75 |
| Petrolatum (white) | 1.00 | — | 0.20 |
| Tricetyl methyl ammonium chloride | 0.50 | 0.50 | 0.50 |
| Ethylene glycol distearate | 0.75 | 0.75 | 0.75 |
| Propylene glycol | 0.50 | 0.50 | 0.50 |
| Lauric monoethanolamide | 3.50 | 3.50 | 3.50 |
| Stearyl stearate | 0.35 | 0.35 | 0.35 |
| Dow-Corning Silicone "B" | 1.00 | 3.00 | 3.00 |

-continued

| Component | Percent (by weight) | | |
|---|---|---|---|
| | A | B | C |
| Sodium chloride | 0.20 | 0.20 | 0.20 |
| Preservative (Germaben II) | 0.50 | 0.50 | 0.50 |
| Sodium citrate or citric acid | 0.01 | 0.01 | 0.01 |
| Aqueous dye solution (0.6% conc.) | 0.31 | 0.31 | 0.31 |
| Perfume | 0.50 | 0.50 | 0.50 |
| | 100.00 | 100.00 | 100.00 |

The compositions of this example are made according to the method described in the previous examples and are evaluated in similar manner. The three shampoos made are effective conditioning shampoos of desired viscosity (4,000 centipoises at 25° C.) and pH (6.5). They are stable on storage and effectively condition hair that is shampooed with them. Shampoos 4/B and 4/C are more effective in improving ease of wet combing than Shampoo 4/A but Shampoo 4/A, despite the fact that it contains less aminosilicone than the other shampoos, is characterized by improved (excellent) dry combing properties. To make shampoo 4/A even more acceptable to consumers the amount of petrolatum in the formula is decreased to 0.75%, to avoid any trace of greasiness in the shampooed hair, and improved and satisfactory conditioning (including superior dry combing ease) are still obtained.

EXAMPLE 5

| Component | Percent (by weight) |
|---|---|
| Deionized water | 73.94 |
| Natrosol 250 HHR' | 0.45 |
| 'Natrosol 330 AP | 0.15 |
| Ammonium lauryl sulfate | 12.50 |
| Sodium lauryl diethoxy sulfate | 2.50 |
| $C_{18-36}$ acid triglyceride | 0.75 |
| Tricetyl methyl ammonium chloride | 0.50 |
| Ethylene glycol distearate | 0.75 |
| Propylene glycol | 0.50 |
| Lauric monoethanolamide | 3.50 |
| Stearyl stearate | 0.35 |
| Aqueous color solution (0.6% conc.) | 0.31 |
| Germaben II | 0.30 |
| Aminosilicone | 3.00 |
| Perfume | 0.50 |
| | 100.00 |

'Hydroxyethyl cellulose (Hercules Corp.)

Shampoos of the above formula are made by the procedure previously described, using different aminosilicones, which shampoos are identified as A, B, C, D and E, and a basic control formula, F, is also made, containing no silicone (but with 3% more deionized water).

Table 2 below identifies the aminosilicones in the various formulas, when present, and Table 3 gives wet combing and dry combing evaluation data for such formulations.

TABLE 2

| Formula Identification | Aminosilicone Identification | Amine Equivalent |
|---|---|---|
| 5/A | A | 4,200 |
| 5/B | B | 30,000 |
| 5/C | C | 2,000 |
| 5/D | D | 2,000 |
| 5/E | E | 1,800 |
| 5/F | F | |

TABLE 3

| Characteristic | Evaluation | | | | | |
|---|---|---|---|---|---|---|
| | 5/A | 5/B | 5/C | 5/D | 5/E | 5/F |
| Wet combing ease | 4.5 | 8.5 | 2 | 1 | 1 | 2.5 |
| Dry combing ease | 4.0 | 8.0 | 2 | 2 | 2 | 2.0 |

From the above data it is seen that some aminosilicones have an adverse affect on hair conditioning or affect it hardly at all whereas those of the present invention, which are components of the A and B compositions, measurably improve conditioning (as measured by eases of wet and dry combing). Such compositions also improve manageability of the hair.

EXAMPLE 6

When, in variations of the formulations of the preceding examples, the various adjuvants are omitted from the formulas so that the shampoos made contain only the required constituents thereof, anionic surfactant(s), cationic surfactant conditioner(s) aminosilicone(s) and water, the preparations made are less viscous than is desirable for commercial shampoos but they are usefully employable for shampooing and conditioning hair. When hydrocarbon components, such as microcrystalline wax and petrolatum, or polyethylene and mineral oil, with paraffin and/or isoparaffin also being addable, are included in the formulations with the basic required components, conditioning is further improved, as was previously indicated.

In the various formulations of the examples other materials mentioned in the specification may be substituted in part for those recited in the examples and useful improvements in hair conditioning (and fiber conditioning) will be obtainable. Thus, triethanolamine lauryl sulfate, sodium myristyl sulfate, potassium cetyl sulfate, triethanolamine myristyl diethoxy sulfate, sodium $C_{14}$ paraffin sulfonate, ammonium $C_{10}$ olefin sulfonate or triethanolamine cocomonoglyceride sulfate, or mixtures thereof, may be employed as the anionic detergent component, and distearyl dimethyl ammonium chloride, trilauryl methyl ammonium chloride, stearyl cetyl dimethyl ammonium chloride or dilauryl diethyl ammonium chloride may be substituted for the cationic surfactant conditioning agent, and improved conditioning will also result. Similarly, various aminosilicones of the formula given and of the mentioned molecular weights and amine equivalents, which describe such polymers, may be employed in place of the specific preferred materials recited herein. Normally, however, it will be preferred to employ those wherein $R^1$, $R^2$, $R^3$, $R^5$, $R^6$ and $R^7$ are alkyls in the lower portion of the 1 to 6 carbon atoms range, such as of two carbon atoms or less and most preferably 1 carbon atom, and $R^8$ is an alkyl group having 3 to 6 carbon atoms with isobutyl being the preferred group. An important consideration in selecting the aminosilicone formulation is the feasibility and economy of its manufacture so the R and other alkyl substituents on the silicon atoms will often be identical, except for $R^4$. As to the adjuvants, different thickeners, viscosity controllers, foaming agents, foam modifiers, stabilizers, dispersing agents, preservatives, pH modifiers, etc. may be substituted for those of the examples, as described in the specification, without interfering with the improved conditioning obtainable. Furthermore, the proportions of components of the compositions of the examples may also be changed, by being increased or decreased by 10%, 20%, 30%, so long as such proportions are retained within the ranges recited in the specification, and in which the mentioned improved conditioning effects are obtainable. Finally, instead of the compositions of the examples all being shampoos they may be employed for cleaning and conditioning other fibrous materials, such as cotton, wool and synthetic fibers, and the formulas may be modified by omission of anionic surfactants to produce non-detersive fiber and hair conditioning preparations that are useful for conditioning previously washed fibers (and which may be employed as hair rinses, mousses or gels to condition washed hair).

The various patent applications, patents and publications previously referred to in this specification are hereby incorporated herein by reference.

The invention has been described with reference to illustrations and examples thereof but is not intended to be limited to these because it is evident that one of skill in the art, with the present specification before him or her, will be able to utilize substitutes and equivalents without departing from the invention.

What is claimed is:

1. A hair conditioning shampoo which is of improved hair conditioning characteristics and does not build up on the hair upon repeated shampooings with it, which comprises 5 to 30% of water soluble synthetic organic anionic detergent, 0.3 to 5% of an aminosilicone of the formula

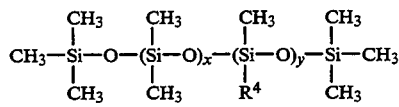

wherein $R^4$ is $-R^8-NH-CH_2CH_2-NH_2$, $R^8$ is alkylene of 3 to 6 carbon atoms, x is an average number in the range of 500 to 10,000, y is 1, which is of an amine equivalent in the range of 10,000 to 40,000, which aminosilicone is in emulsion or dispersion form in the shampoo, 0.1 to 5% of cationic surfactant hair conditioning agent and 50 to 95% of water.

2. A hair conditioning shampoo according to claim 1 which comprises 5 to 30% of water soluble synthetic organic anionic detergent selected from the group consisting of sulfate detergent, sulfonate detergent and mixtures thereof, 0.3 to 5% of the aminosilicone, 0.1 to 5% of the cationic surfactant which comprises a quaternary ammonium salt cationic surfactant hair conditioning agent of the formula $R^9$ $R^{10}$ $R^{11}$ $R^{12}$ $N+$ $X-$, wherein $R^9$ is lower alkyl of 1 to 4 carbon atoms, $R^{10}$ and $R^{11}$ are higher alkyls of 10 to 40 carbon atoms, $R^{12}$ is such a lower alkyl or such a higher alkyl, and $X-$ is a salt forming anion, 50 to 95% of water, and which further comprises 0.1 to 30% of adjuvants for the shampoo.

3. A hair conditioning shampoo according to claim 2 which comprises 8 to 25% of the water soluble synthetic organic anionic detergent(s), which is of 8 to 20 carbon atoms in the lipophile group(s) thereof, 0.5 to 5% of the aminosilicone, 0.1 to 3% of said quaternary ammonium salt wherein X in the formula given is a halogen which is chlorine, bromine or iodine or any mixture thereof, and the sum of the numbers of carbon atoms is at least 30, 0.5 to 20% of said adjuvants and 60 to 90% of water.

4. A hair conditioning shampoo according to claim 3 which comprises 10 to 20% of the water soluble synthetic organic anionic detergent(s), 0.8 to 4% of the aminosilicone, 0.2 to 2% of the quaternary ammonium halide wherein the halogen is chlorine or bromine or a mixture thereof, 3 to 15% of adjuvants and 65 to 80% of water, which shampoo is of a viscosity in the range of 1,500 to 10,000 centipoises at 25° C.

5. A hair conditioning shampoo according to claim 4 which comprises 12 to 18% of the water soluble synthetic organic anionic detergent, which detergent is selected from the group consisting of alcohol sulfates of 10 to 18 carbon atoms in the alkyl thereof, alcohol ether sulfates of 10 to 18 carbon atoms in the alkyl thereof and of 1 to 3 ethoxy groups in the ether portion thereof, or any mixture thereof, wherein the cations of such detergent salts are alkali metal, ammonium or lower alkanolamine of 1 to 3 carbon atoms in the alkanol, or any mixture thereof, 1 to 3% of the aminosilicone, 0.3 to 1% of the quaternary ammonium halide, in which the halogen is chlorine and $R^{12}$ is higher alkyl, 3 to 15% of adjuvants, and 65 to 80% of water, which shampoo is of a viscosity in the range of 3,000 to 6,000 centipoises at 25° C. and is of a pH in the range of 5 to 8.

6. A hair conditioning shampoo according to claim 5 which comprises about 13% of ammonium lauryl sulfate, about 3% of sodium lauryl diethoxy sulfate, about 3% of the described aminosilicone, in which $R^4$ of the formula is $R^8-NH-CH_2-CH_2-NH_2$ and $R^8$ is isobutyl, about 0.5% of tricetyl methyl ammonium chloride, about 8% of adjuvants and about 73% of water, in which the viscosity is in the range of about 3,500 to 4,000 centipoises at 25° C. and the pH is in the range of about 6 to 7.

7. A process for shampooing and conditioning hair which comprises applying to such hair a conditioning proportion of a composition according to claim 1 in such manner as to distribute such composition over such hair.

8. A process according to claim 7 herein the shampooing and conditioning composition is a shampoo which comprises 5 to 30% of water soluble synthetic organic anionic detergent selected from the group consisting of sulfate detergent, sulfonate detergent and mixtures thereof, 0.3 to 5% of the aminosilicone, 0.1 to 5% of quaternary ammonium salt cationic surfactant hair conditioning agent of the formula $R^9$ $R^{10}$ $R^{11}$ $R^{12}$ $N+$ $X-$, wherein $R^9$ is lower alkyl of 1 to 4 carbon atoms, $R^{10}$ and $R^{11}$ are higher alkyls of 10 to 40 carbon atoms, $R^{12}$ is such a lower alkyl or such a higher alkyl, and $X-$ is a salt forming anion, 0.1 to 30% of adjuvants for the shampoo, and 50 to 95% of water, the application of the shampooing and conditioning composition to the hair is by shampooing of the hair, and such application is followed by rinsing and drying of the shampooed and rinsed hair, and by wet or dry combing thereof.

9. A process according to claim 8 wherein the shampoo comprises about 13% of ammonium lauryl sulfate, about 3% of sodium lauryl diethoxy sulfate, about 3% of the aminosilicone, in which $R^4$ of the formula is $-R-$$^8-NH-CH_2-CH_2-NH_2$ and $R^8$ is isobutyl, about 0.5% of said quaternary ammonium salt which comprises tricetyl methyl ammonium chloride, about 8% of adjuvants and about 73% of water, in which shampoo the viscosity is in the range of about 3,500 to 4,000 centipoises at 25° C. and the pH is in the range of about 6 to 7, the shampoo is applied to hair on the human head at the rate of 2 to 15 grams per shampooing, is maintained in contact with the hair, as an aqueous foam, for from 1 to 5 minutes, and is rinsed off, after which the hair is wet combed, blow dried and dry combed.

10. A process according to claim 8 wherein the amine equivalent of the aminosilicone is about 30,000.

11. A shampoo according to claim 1 wherein $R^8$ is an isobutyl group, the average x is in the range of 750 to 800, the amine equivalent of the aminosilicone is about 30,000 and the aminosilicone is in dispersed or emulsified state in the shampoo and the shampoo is stable on storage, without settling out of components thereof and without phase separation occurring.

12. A hair conditioning shampoo according to claim 1 which said adjuvant further comprises 0.5 to 20% of a hydrocarbon or a mixture of hydrocarbons selected from the group consisting of normally solid polyethylene, mineral oil, paraffin, isoparaffin, petrolatum and microcrystalline wax.

13. A hair conditioning shampoo according to claim 2 which said adjuvant further comprises 0.1 to 3% of microcrystalline wax and 0.1 to 2% of paraffin.

14. A hair conditioning shampoo according to claim 3 which further comprises 0.5 to 2% of microcrystalline wax and 0.5 to 1.5% of paraffin.

15. A hair conditioning shampoo according to claim 1 which further comprises 0.2 to 5% of a normally solid polyethylene and 0.1 to 10% of a normally liquid mineral oil, which mineral oil makes the polyethylene water dispersible, emulsifiable or soluble, and increases its hair conditioning effects.

16. A hair conditioning shampoo according to claim 2 which said adjuvant further comprises 0.2 to 2% of a normally solid polyethylene and 0.2 to 8% of a normally liquid mineral oil, which mineral oil makes the polyethylene water dispersible, emulsifiable or soluble.

17. A process according to claim 9 wherein said adjuvant in the hair conditioning shampoo further comprises 0.5 to 2% of microcrystalline wax and 0.5 to 1.5% of paraffin.

18. A process for the manufacture of a stable hair conditioning shampoo of the composition of claim 1 which comprises admixing the components, except for the aminosilicone, and heating to an elevated temperature at which the aminosilicone, when heated, will form an emulsion or stable dispersion when admixed with such composition and subsequently cooled, heating the aminosilicone and mixing the aminosilicone and the composition, less aminosilicone, for from one minute to one hour to disperse the aminosilicone in the composition, and cooling the composition to stable emulsion or dispersion form.

19. A process for the manufacturer of a stable hair conditioning shampoo of the composition of claim 6 wherein the polyethylene and mineral oil are heated together to a temperature in the range of 70° to 90° C. to melt, dissolve or disperse the polyethylene in the mineral oil, the balance of the composition components except for the aminosilicone, is processed to dispersion or emulsion form by mixing together the components thereof and heating to a temperature in the range of 70° to 90° C., the two such pre-mixes are admixed at such elevated temperature and the aminosilicone, at a temperature in the range of 70° to 90° C., is admixed with the combination of pre-mixes, and the mix is cooled to room temperature, to produce a stable hair conditioning shampoo, which does not deteriorate, separate or settle out on storage before use.

* * * * *